United States Patent [19]

Smid

[11] Patent Number: 4,783,282
[45] Date of Patent: Nov. 8, 1988

[54] DETERGENTS CONTAINING POLYETHER CARBOXYLIC ACID DERIVATIVES, THEIR PREPARATION AND THEIR APPLICATION

[75] Inventor: Jacob K. Smid, Doetinchem, Netherlands

[73] Assignee: Stamicarbon B.V., Geleen, Netherlands

[21] Appl. No.: 907,356

[22] Filed: Sep. 15, 1986

[30] Foreign Application Priority Data

Sep. 20, 1985 [NL] Netherlands ............... 8502587

[51] Int. Cl.$^4$ ................... C11D 1/10; C11D 1/83
[52] U.S. Cl. .................. 252/546; 252/89.1; 252/174.18; 252/174.21; 252/544; 252/548
[58] Field of Search ......... 252/546, 544, 142, 174.18, 252/525, 174.21; 562/567; 260/404

[56] References Cited

U.S. PATENT DOCUMENTS 2,151,788   3/1939   Mauersberger ............... 260/404
4,307,079   12/1981  Zorayan et al. ............... 424/70

FOREIGN PATENT DOCUMENTS 102118   3/1984   European Pat. Off. .
154380   9/1985   European Pat. Off. .
2644498  4/1978   Fed. Rep. of Germany .

OTHER PUBLICATIONS

Hydrolysis of Fats, Saponification, Soap, Organic Chemistry, 2nd Edition, Robert T. Morrison and Robert N. Boyd, pp. 685–686, 1966.
Polyoxyethylene Esters of Fatty Acids, Nonionic Surfactants, Martin T. Schick, pp. 142–146, Marcel Dekker, Inc., New York, 1967.
European Search Report EP 86 20 1588 dated Oct. 12, 1986.

*Primary Examiner*—Paul Lieberman
*Assistant Examiner*—Hoa Van Le
*Attorney, Agent, or Firm*—Cushman, Darby & Cushman

[57] ABSTRACT

The invention relates to a process for the preparation of a detergent containing one or more compounds having the formula $RCONH(C_2H_4O)_nCH_2COOH$, salts and glycerol, ethoxylated glycerol, carboxymethylated glycerol, or carboxymethyl ethoxylated glycerol and mixture thereof, where R represents a linear or branched aliphatic hydrocarbon group with 5–21 carbon atoms and n is a number from 1–20, by amidating, ethoxylating and carboxymethylating one or more fatty acids having the formula RCOOH and, if so desired, converting all or part of the ether carboxylic acid obtained to a salt thereof, characterized in that an oil or fat is started from and that this oil or fat is aminolyzed in the presence of an alkali(ne earth) metal and the reaction mixture obtained is in the usual manner ethoxylated, carboxymethylated and, if desired, converted in whole or in part to a salt.

7 Claims, No Drawings

DETERGENTS CONTAINING POLYETHER CARBOXYLIC ACID DERIVATIVES, THEIR PREPARATION AND THEIR APPLICATION

The invention relates to a process for the preparation of a detergent containing one or more compounds having the formula $RCONH(C_2H_4O)_nCH_2COOH$ and/or salts thereof, R being a linear or branched aliphatic hydrocarbon group with 5-21 carbon atoms and n a number from 1-20, by amidating, ethoxylating and carboxymethylating one or more fatty acids having the formula RCOOH and, if so desired, converting all or part of the ether carboxylic acid obtained to a salt thereof.

Such a process is known from Applicant's patent application EP-A-102118. The compounds started from, the fatty acids having the formula RCOOH, are usually prepared from oils or fats, in particular when R represents an aliphatic group with 10-20 carbon atoms. The oils and/or fats are saponified according to generally known methods, and the fatty acids formed are separated from the reaction mixture. As is generally known, oils and fats consist to a considerable extent of glycerol esters of fatty acids, so that in the saponification product considerable amounts of glycerol are present. On account of the high boiling point and the high viscosity of glycerol, its separation from the fatty acids is cumbersome and expensive. It was assumed that the presence of glycerol would interfere with the ethoxylation and carboxymethylation of the fatty acids, or would at least lead to products with less desirable properties.

Surprisingly, it was found that aminolysis of oils or fats with monethanolamine in the presence of an alkali(ne earth) metal alkylate followed by ethoxylation and carboxymethylation of all of the reaction product yields a mixture which has extremely favourable properties as a washing agent, in terms of washing properties as well as tolerability for hair and skin. Therefore, such a product is particularly suitable for use in detergents intended for frequent and prolonged contact with the human skin or with human hair, e.g. shampoos, shower and bath preparations, skin-care products such as creams, cleaning agents for dishwashing and other agents for manual cleaning and such like.

In the framework of this invention, aminolysis means conversion of the relevant fatty acid esters with monoethanolamine to fatty acid monoethanolamides and glycerol.

It has been found that coconut oil, a cheap product, leads to an excellent product.

The invention also relates to the detergents obtainable according to the invention, and to their use, and to washing or cleaning agent preparations containing the detergents in question.

For the preparation of the detergents according to the invention a fat or an oil, preferably coconut oil, may be started from. If coconut oil is started from, it may be refined or unrefined.

The oil is aminolysed with monoethanolamine in the presence of an alkali(ne earth) metal alkylate. Preferably, sodium methylate is used. Application of monoethanolamine is advantageous in that the aminolysed product obtained already has a hydroxyethyl group attached to the amido-nitrogen atom. Of course, the amidation can, in principle, be carried out also with ammonia, after which, in the subsequent ethoxylation, one ethoxy group more must be introduced, but from a technical point of view the use of monoethanolamine is much simpler than using the toxic and pressurised ammonia. The reaction can be conducted at an elevated temperature (e.g. 50°-100° C.) and in a relatively short time (1 to a few hours). Since the process preferably takes place at an elevated temperature, the physical state of the oil started from is not important, which means that the oil may also be solid or semi-solid at ambient temperature.

The reaction mixture obtained contains free glycerol and monoethanolamide of the fatty acids of the coconut oil and possibly also free fatty acid, and in addition by-products, whether or not converted, from the original coconut oil.

This mixture is now ethoxylated in the usual manner. As is known, this yields a reaction mixture with a varying number of ethoxy groups per molecule. The reaction is usually conducted at a temperature of the order of 125° C. (in general 100°-150° C.).

Ethoxylation can of course occur at the hydroxyl group of the monoethanolamide, but also at one or more hydroxyl groups of the glycerol, while the by-products, which are present in relatively small amounts, can also be subject to ethoxylation.

The product thus obtained is carboxymethylated, again in the usual manner, as described in e.g. EP-A-102118, usually with sodium chloroacetate and at an elevated temperature. Thus a crude reaction mixture is obtained, in which the carboxymethyl groups are, of course, present further in different ways, for example as follows:

(a) The crude reaction mixture is diluted with water to 30% dry solids and the pH is set to 7, preferably with hydrochloric acid. The product then still contains NaCl and other impurities. NaCl is often used as a thickening agent in cosmetic products. The product thus obtained is found to perform very well in shampoos and the like.

(b) The product is washed with water and hydrochloric acid by heating a mixture of water and hydrochloric acid to, for example, 90° C. and then adding the crude reaction mixture, allowing the solution to stand and separating the layers. The oil layer is recovered and contains the carboxymethylation products in the form of free acid. The product thus purified can now be converted to sodium salt with sodium hydroxide solution at about 50° C.

Further, it is customary to add a preservative to the endproduct, e.g. benxylformal.

During ethoxylation and carboxymethylation, many different hydrophylic compounds can be formed. Applicant has found that, although the compositions started from are not fully defined, reproducible results are obtained and, as already mentioned, the mixtures obtained have excellent cleaning properties and are well tolerated by the human skin and human hair.

The product of the invention contains a certain amount of carboxylic amide derivatives according to EU-A-0102108, so that in choosing the number of ethoxy units to be introduced one will, as usual, take into consideration the nature of the hydrophobic radicals of the fatty acids of which the oils and fats used as starting materials are composed. Higher fatty acids (e.g. $C_{18}$) in general tend to require more ethoxy units than lower ones ($C_{12}$–$C_{14}$), but for all these hydrophobic radicals a broad range of ethoxy units can be used. In general, the number of ethoxy units to be introduced is 0-19 (assuming that amidation has been performed with ethanolamine).

In the above discussion of the general procedure of the process, in the section on carboxymethylation, the eventual preparation of a sodium salt was mentioned. Of course, when proceeding via the free acid, also other salts can be prepared, with alkali metals, alkaline earth metals (thanks to their low sensitivity to calcium) and ammonium and amines.

The choice of applicable oils and fats is very wide, and in general all vegetable and animal oils and fats are suitable as starting products. Of course, with some products the presence of impurities with an unpleasant odour can be an impediment, and further the choice will often be determined mainly by price and availability. Finally, it is of course possible to mix different types of oils and/or fats, if so desired, and to use these mixtures as starting products.

As already mentioned, the products under consideration combine excellent cleaning activity with a good tolerability to skin and hair. Of course, in quantitative terms these properties depend to some extent on the combination of oil and/or fat chosen and the average number of ethoxy units introduced by the ethyoxylation, but by the usual tests a person skilled in the art can easily determine optimum combinations.

The invention will be explained below with reference to a number of preparations and formulations.

EXAMPLE I

Step A 510.6 g crude (unrefined) coconut oil used as starting material was melted at 35° C., after which 138.8 of monoethanolamine (according to calculations about 1.02 mole equivalents, referred to the coconut oil) and 5.1 g of a solution of 30% NaOCH$_3$ in methanol were added, in that order. Next, the mixture was heated at 60°-70° C. for two hours with stirring and afterwards allowed to stand for four hours at 70° C., after which it had become clear. It was then allowed to after-react for a short time at 75° C. The yield was 654.2 g.

Step B

To the product of step A, on average three ethoxy units were added, as follows:

In about 15 minutes 249 g of epoxyethane was led into 546.6 g of the product obtained according to I-A, which contained 89.4% monoethanolamide of coconut acid, at a temperature of 117°-127° C. and a pressure of 0.2-8 atmospheres. The reaction proceeded readily, and afterwards stirring was continued for another 30 minutes, the mixture being cooled to 70° C. The yield of ethoxylated product was 790.3 g.

Step C 674.7 g of the product obtained according to step B was reacted with 281.7 g of sodium monochloroacetate and 96.7 g of solid NaOH. The carboxymethlyation was conducted in the usual manner, for a period of 6 hours. This yielded 1038.7 g of crude reaction mixture.

Step C-1

203.8 g of the crude reaction mixture obtained in step C was dissolved in 400 g of water, and 0.9 g of preservative (benzylformal) was added. The pH was lowered to 7.0 with 9.8 of 10% HCL. the mixture was then diluted to 679.3 g with water (concentration 30%). The product so obtained could be used as such.

Step C-2

834.9 g of the crude reaction mixture was washed with 754.7 g of water and 197.8 g of 30% hydrochloric acid. This was done in a three-liter glass beaker equipped with a thermometer and a stirrer. After separation of the layers, 438.9 g of product in the form of free acid was obtained. In a two-liter glass beaker equipped with a thermometer and a stirrer, 339.0 g of this product was added to a mixture of 600 g of water and 38.4 g of 50% NaOH, which mixture was heated at 50° C. Afterwards, another 2.3 g of 50% NaOH and 1.5 g of benzylformal were added. Finally, 8.3 g of 10% HCL was added to lower the pH from 8.2 to 7.1. The end-product was diluted to 1055.9 g with water.

EXAMPLE II

Step A 1096.6 g of refined coconut oil was melted at 35° C. Next, 315.9 g of monoethanolamine (according to calculations 1.02 equivalents) and 11.0 g of 30% NaOCH$_3$ in methanol were added, in that order. The mixture was heated at 60°-70° C. for about 20 minutes, after which it was clear. Afterwards, the mixture was still allowed to after-react at 70° C. for 90 hours. A small portion of the mixture was allowed to after-react at 105° C., which was found to be a much more rapid process, as expected. However, after-reaction at 70° C. can in practice be carried out simply in a temperature-controlled storage vessel, no further labour being required, so that, for the present, after-reaction at this temperature is considered to be preferable.

Step B

To the product obtained according to step A, on average 9 ethoxy units were added, as follows: In 40 minutes, 560 g of epoxyethane was led into 391.5 g of the product of step A, at a temperature of 112°-130° C. and a gauge pressure of 0.2-8 atmospheres. This yielded 950 g of product.

Step C 402.2 g of the product of step B was transferred to a 1 liter glass beaker which was equipped with a thermometer and a stirrer and was placed in a water bath, and 109.8 g of sodium monochloroacetate and 37.7 g of solid NaOH were added. The reaction was conducted for 6 hours, at 60°-75° C. This yielded 543.2 g of product.

Step C-1

203.6 g of this product was dissolved in 400 g of water, after which 0.9 g of benxylformal was added and the pH was lowered to 7.0 with 4.9 of 30% HCL. Afterwards, the mixture was diluted to 678.7 g with water, to yield a clear brown liquid with a viscosity of 5.8 mPa.s at 22° C. and a pH of 7.0. The solids content was 30%.

Step C-2

In a two-liter glass worker beaker equipped with a stirrer and a thermometer, 339.6 g of the crude reaction mixture of th carboxymethylation was neutralised with 225.6 g of water and 77.8 g of 30% HCL, at a temperature of 85°-90° C.

260 g of water and 18.0 g of 50% NaOH were transferred to a two-liter glass beaker equipped with a stirrer and a thermometer and were heated to about 50° C. Then 164.5 g of the oil layer obtained in the neutralization described above was added. Finally, another 1.7 g of NaOH and 0.8 g of benzylformal were added, and the mixture was diluted with 491.0 g of water to obtain 676.5 g of solution with a solids content of 22%. The clear product obtained had a viscosity of 11.5 mPa.s at 20° C. and a pH of 7.2.

To the examples above, the following comments are given here:

1. In step A, the saponification number of the oil was determined beforehand, so that the average molecular weight of the fatty acids presents was known. On the basis of this, monoethanolamine can be dosed.

2. The reaction mixture obtained according to step A still contains sufficient alkali to serve as an ethoxylation catalyst. For this reason no catalyst was added. If it is desired to use SbCl$_5$ as a catalyst, the mixture must first be neutralised, of course, and therefore this process mode, though feasible, is not preferred.

EXAMPLE III

This example shows the preparation of a product as in Example I on a technical scale.

Step A 1000 kg of refined coconut oil used as starting product was heated to 32° C. to melt it. In 7 minutes, 283 kg of monoethanolamine was added, and then, in one go, 10 kg of 30% sodium methylate. Next, the mixture was heated to 60° C. in 10 minutes, after which the temperature quickly and spontaneously rose to 80° C. and was kept constant at that value for about 15 minutes by cooling. Then the cooling and the stirrer were stopped and the mixture was allowed to stand at 72°-78° C. After a total reaction time of 24 hours the reaction had been completed. The yield was 1250 kg (theoretically 1293 kg; losses occur during discharge etc.).

Note: In this large-scale test run, the whole amidation process was conducted in the reactor, but in practice the complete mixture can also be pumped to a heated storage tank and allowed to react further, when cooling is no longer necessary.

Step B 1246 kg of the product of step A was transferred to a clean and dry reactor, under partial vacuum and at a temperature of 85° C. After 20 minutes, the mixture was heated further and when after another 20 minutes a temperature of 115° C. was reached epoxyethane dosing was started. The reaction temperature was 120°-130° C. In all, 587 kg of epoxyethane (corresponding to an average addition of three ethoxy units) was added in 15 hours. After the mixture had reacted for another half hour, it was cooled to 78° C. in 15 minutes. A product with a melting point of 16° C. and an $N_D^{25}=1.4469$ was obtained. The product was divided between ten different containers, the total yield being 1813 kg (theoretically 1833 kg; losses occur during filling of the containers).

Step C 1800 kg of the product of step B was reacted with 762 kg of sodium monochloroacetate in the presence of 4 kg of sodium chloride and 262 kg of solid NaOH. The reaction was carried out as follows: the 1800 kg of product was transferred to the reactor and heated to 50° C. in 10 minutes. After sampling of the product, 62 kg of the sodium monochloro-acetate and the 4 kg of sodium chloride were added, in that order, while heating was continued. After 10 minutes the temperature had risen to 66° C. and the heating was stopped. At that point, the addition, in portions, of the rest of the sodium monochloroacetate and the simultaneous addition of the NaOH prills started. These materials were added in 10 portions, at half-hour intervals (ten times 70 kg of sodium monochloro-acetate and twice 27 and eight times 26 kg of NaOH). Towards the end of the addition, the mixture clearly thickened. The temperature was kept between 65° and 75° C. all the time. After the last addition, the mixture was allowed to after-react for another hour at 70° C. Afterwards, 3 kg of 30% hydrogen peroxide was added and the product was briefly heated at 90° C.

Step C-2

2780 of the crude reaction mixture obtained was acidified as follows: A mixture of 2536 kg of softened water and 780 kg of 30% HCL was heated to 90° C. In half an hour, the crude reaction mixture obtained as described above was added, during which addition at first some foaming occurred. Twenty minutes later, a sample was found to have a pH of 2.8. At 15-minute intervals, another three portions of 50 kg of 30% HCL were added, and the pH was eventually found to have decreased to 1.7. Stirring was stopped, and the layers were separated. The upper, organic layer is the desired product, which contains 10.6% of residual water and has a melting point of 10° C. 1440 kg of this organic phase was transferred to a reactor, and in half an hour 2750 kg of water and 180 kg of 50% NaOH were added. Afterwards, a sample was found to have a pH of 7.1. After another 40 minutes, 170 kg of water was added and the mixture was heated to 60°-70° C. After half an hour the mixture, which now had a paler colour, was slowly cooled to 50° C. 5 kg of benzylformal (30%) was added, and the mixture was allowed to stand overnight and then discharged into containers. In all, 4560 kg of neutral product was obtained, with a viscosity of 1700 mPa.s at 20° C. The product had a pale colour.

EXAMPLE IV

Liquid soap

Two liquid soap preparations were prepared:

| Component | a (%) | b (%) |
| --- | --- | --- |
| (1) Na—laurylethersulphate (2 ethoxy units, concentration 28%) | 48.00 | 53.00 |
| (2) mother-of-pearl concentrate[a] | 6.00 | — |
| (3) Na—alkylethercarboxylate, 22% solution in water[b] | 7.00 | 7.00 |
| (4) product of Example II (step C-2) | 11.00 | 11.00 |
| (5) benzylformal | 0.07 | 0.07 |
| (6) colorant | q.s. | q.s. |
| (7) perfume | q.s. | q.s. |
| (8) NaCl | 2.26 | 2.66 |
| (9) water | 25.67 | 26.27 |
| | 100.00% | 100.00% |

[a]a mixture of sodium laurylethersulphate, fatty acid diethanolamide and glycoldistearate in water. 11 parts by weight of glycoldistearate in water.
[b]lauryl-myristyl (70:30) —O(C$_2$H$_4$O)$_{10}$—CH$_2$COONa, neutralised.

Instead of 11% of the product of Example II, in these formulations also 8% of the product of Example I can be used, with a correspondingly larger amount of water.

The liquid soap was prepared by adding the components 2,3,4 and 5, in that order, to component 1), while stirring. The NaCl was dissolved in water and added to the pre-mix obtained. The mixture was stirred until it was homogenous, and colorant and perfume were added at will, and the remaining amount of water was also added.

The two products had a concentration of surfactant of about 20%; the pH was set to about 7-7.5 and the viscosity at 20° C. was >3000 mPa.s for product a and 2000 mPa.s for product b. The liquid soaps obtained had a very good foaming behaviour and foam stability, also in cold water, and possessed good dermatological properties.

Note: preparations with the mother-of-pearl concentrate should have a viscosity of at least 3000 mPa.s at 20° C.

EXAMPLE V

Recipe for foam bath

| Component | % |
|---|---|
| (1) Na—laurylethylsulphate (2 ethoxy groups, concentration 28%) | 52.00 |
| (2) product of Example II (step C-2) | 10.00 (or 8% of product of Example I, step C-2) |
| (3) Na—alkylethercarboxylate (same as in Example I) | 6.00 |
| (4) thickening agent[a] | 2.00 |
| (5) Akypoquat 132[b] | 2.50 |
| (6) Benzylformal | 0.07 |
| (7) perfume | q.s. |
| (8) colorant | q.s. |
| (9) water | make-up to 100% |

[a]RO—(CH$_2$CH$_2$O)$_{1.5}$CH$_2$CO—NH—CH$_2$CH$_2$OH; R is a rest group from a synthetic C$_{12}$/C$_{13}$ alcohol mixture; thickening agent according to Patent Application No. 8402893.
[b]Product of the reaction between lauric acid and glycidyltrimethylammonium chloride; this quaternary product makes the tactile properties even better.

EXAMPLE VI

Recipe for shower preparation

| Component | % |
|---|---|
| (1) Sodium laurylethersulphate (same as Example IV) | 40.00 |
| (2) mother-of-pearl concentrate (see Example IV) | 6.00 |
| (3) product of Example I | 14.00 (or 19.00% of product of Example II, step C-2) |
| (4) thickening agent, see Example V | 2.00 |
| (5) benzylformal | 0.07 |
| (6) NaCl | 0.60 |
| (7) perfume | q.s. |
| (8) colorant | q.s. |
| (9) water | make-up to 100% |

EXAMPLE VII

Recipe for shampoos for dry hair

| Component | % |
|---|---|
| (1) Na—laurylethersulphate (see Example IV) | 40.00 |
| (2) product of Example I | 7.00 (or 9.00% of product of Example II, step C-2) |
| (3) mother-of-pearl concentrate (see Example IV)[a] | 5.00 |
| (4) Akypoquat 132[b] | 0.50 |
| (5) benzylformal | 0.07 |
| (6) perfume | q.s. |
| (7) colorant | q.s. |
| (8) NaCl | 2.80 |
| (9) water | make-up to 100% |

[a]By adding this product an emulsified shampoo is obtained; if this component is omitted a clear shampoo is obtained.
[b]this component has a conditioning effect (with regard to the 'feel' of the hair and anti-static properties).

EXAMPLE VIII

The procedure was the same as in the Examples I and II, but the product started from was castor oil, while in step B on average 10 ethoxy units were added.

In step A, 203.3 g of castor oil (liquid at room temperature), 38.7 g of monoethanolamine and 2 g of 30% sodium methylate in methanol were started from. Owing to the reaction the temperature of the mixture rose to 32° C., and the mixture was afterwards allowed to after-react for one week in a storage vessel, at 40° C.

In step B, 204 g of the product obtained was reacted with 230 g of epoxyethane, proceeding as in the Examples I and II. Also step C, the carboxymethylation step, was carried out in the same way. The yield was 460 g of crude reaction mixture, which was acidified with hydrochloric acid and water according to step C-2. This yielded 410 g of oil, which in this case was the end product. The oil can be used as a component in any of the examples IV-VII, if necessary together with a neutralising agent.

I claim:

1. Process for the preparation of a composition containing one or more compounds having the formula RCONH(C$_2$H$_4$O)$_n$CH$_2$COOH, salts glycerol, ethoxylated glycerol, carboxymethylated glycerol, or carboxymethyl ethoxylated glycerol and mixture thereof, where R represents a linear or branched aliphatic hydrocarbon group with 5-21 carbon atoms and n is a number from 1-20, comprising the following steps:
   (a) aminolysing oil or fat starting materials in the presence of an alkaline (earth) metal alkylate resulting in a mixture including amides of fatty acids having the formula RCOOH, where R represents a linear or branched aliphatic hydrocarbon group with 5-21 carbon atoms, and glycerol;
   (b) ethoxylating the product resulting from step (a);
   (c) carboxymethylating the product resulting from step (b); and
   (d) processing the reaction mixture resulting from step (c) into a product which contains aminolysed, ethoxylated and carboxymethylated compounds resulting from steps (a), (b) and (c) and/or salts thereof.

2. Process according to claim 1, wherein step (a), said alkaline (earth) metal alkylate is sodium methylate.

3. Process according to claim 1 wherein step (a), said aminolysing is conducted at a temperature of 50°-100° C.

4. Process according to claim 1, wherein step (a) said starting material is coconut oil.

5. A composition containing one or more compounds having the formula RCONH(C$_2$H$_4$O)$_n$CH$_2$COOH, salts glycerol, ethoxylated glycerol, carboxymethylated glycerol, or carboxymethyl ethoxylated glycerol and mixture thereof, where R represents a linear or branched aliphatic hydrocarbon group with 5-21 carbon atoms and n is a number from 1-20, resulting from the process comprising the following steps:
   (a) aminolysing oil or fat starting materials in the presence of an alkaline (earth) metal alkylate resulting in a mixture including amides of fatty acids having the formula RCOOH, where R represents a linear or branched aliphatic hydrocarbon group with 5-21 carbon atoms, and glycerol;
(b) ethoxylating the product resulting from step (a);
(c) carboxymethylating the product resulting from step (b); and
(d) processing the reaction mixture resulting from step (c) into a product which contains aminolysed, ethoxylated and carboxymethylated compounds resulting from steps (a), (b) and (c), and/or salts thereof.

6. Washing or cleaning agent preparation containing a detergent according to claim 5.

7. Process according to claim 1 wherein the number of ethoxy units introduced in step (a) and step (b), total from 1 to 20.

* * * * *

UNITED STATES PATENT AND TRADEMARK OFFICE
CERTIFICATE OF CORRECTION

PATENT NO. : 4,783,282

DATED : November 8, 1988

INVENTOR(S) : SMID, Jacob K.

It is certified that error appears in the above-identified patent and that said Letters Patent is hereby corrected as shown below:

Column 8, line 29, after "of a" insert --detergent--;

column 8, line 31, after "salts" insert --thereof and--;

column 8, line 33, replace "mixture" with --mixtures--;

column 8, line 58, after "A" insert --detergent--;

column 8, line 59, after "salts" insert --thereof and--;

column 8, line 62, replace "mixture" with --mixtures.

Title page:

Abstract [57], line 12, after "salt" insert --thereof and; and line 14, replace "mixture" with --mixtures--.

Signed and Sealed this

Fourteenth Day of August, 1990

Attest:

HARRY F. MANBECK, JR.

*Attesting Officer*        *Commissioner of Patents and Trademarks*